United States Patent
McMenamin et al.

(10) Patent No.: US 10,493,231 B2
(45) Date of Patent: Dec. 3, 2019

(54) CURVED URINARY CATHETER

(71) Applicant: Hollister Incorporated, Libertyville, IL (US)

(72) Inventors: Martin McMenamin, Lifford (IE); Marine Veronique Germaine Richard, Carrieres sur Seine (FR); Adam J. Foley, Swords (IE)

(73) Assignee: Hollister Incorporated, Libertyville, IL (US)

( * ) Notice: Subject to any disclaimer, the term of this patent is extended or adjusted under 35 U.S.C. 154(b) by 275 days.

(21) Appl. No.: 15/511,716

(22) PCT Filed: Sep. 16, 2015

(86) PCT No.: PCT/US2015/050357
§ 371 (c)(1),
(2) Date: Mar. 16, 2017

(87) PCT Pub. No.: WO2016/044379
PCT Pub. Date: Mar. 24, 2016

(65) Prior Publication Data
US 2017/0291011 A1    Oct. 12, 2017

Related U.S. Application Data

(60) Provisional application No. 62/051,666, filed on Sep. 17, 2014.

(51) Int. Cl.
*A61M 25/00* (2006.01)
*A61M 27/00* (2006.01)
*A61M 25/01* (2006.01)

(52) U.S. Cl.
CPC ...... *A61M 25/0017* (2013.01); *A61M 25/002* (2013.01); *A61M 25/0111* (2013.01);
(Continued)

(58) Field of Classification Search
CPC ............ A61M 25/0017; A61M 25/002; A61M 25/0113; A61M 27/008; A61M 25/0111;
(Continued)

(56) References Cited

U.S. PATENT DOCUMENTS 1,194,735 A * 8/1916 Hendricks .......... A46B 11/0093
                                                  15/248.1
2,310,571 A * 2/1943 Brady .................... A45D 44/18
                                                  401/124
(Continued)

FOREIGN PATENT DOCUMENTS

CN          2078634 U      6/1991
WO    WO 2004/054653      7/2004
(Continued)

OTHER PUBLICATIONS

International Search Report and Written Opinion of the International Searching Authority for International Application No. PCT/US2015/050357 dated Mar. 15, 2016.
(Continued)

*Primary Examiner* — Adam Marcetich
(74) *Attorney, Agent, or Firm* — Cook Alex Ltd.

(57) ABSTRACT

A catheter assembly including curved urinary catheter and a similarly curved housing for holding and carrying the same are disclosed. A catheter subassembly may be removed from the housing and mounted onto the handle to provide the catheter assembly in an extended deployed condition. The insertable portion of the catheter is curved in a way that compliments the curvature of the female urethra.

16 Claims, 3 Drawing Sheets

(52) U.S. Cl.
CPC ........ *A61M 25/0113* (2013.01); *A61M 27/00* (2013.01); *A61M 27/008* (2013.01); *A61M 25/0009* (2013.01)

(58) Field of Classification Search
CPC .......... A61M 25/0009; A61M 2209/06; A61M 2210/1078; A61M 2210/1089; A61M 2210/1092; A61M 25/0041; A45D 44/18; A46B 7/023; A46B 7/026; A61B 1/00142; A61B 1/00144; A61B 2050/3005; A61B 2050/3006; A61B 2050/3009; A61B 2050/3014; A61B 50/30; A61F 2/04
See application file for complete search history.

(56) References Cited

U.S. PATENT DOCUMENTS

| | | | | |
|---|---|---|---|---|
| 2,318,171 | A * | 5/1943 | Lipic, Jr. | B43K 23/00 401/88 |
| 2,701,381 | A * | 2/1955 | Lodewick | A46B 5/0095 15/184 |
| 2,835,246 | A * | 5/1958 | Boettger | A61B 10/0096 600/570 |
| 3,369,542 | A | 2/1968 | Thaidigsman | |
| 3,755,848 | A * | 9/1973 | Mutrie | A46B 5/0095 15/184 |
| 3,867,945 | A | 2/1975 | Long | |
| 3,920,023 | A | 11/1975 | Dye | |
| 4,152,804 | A * | 5/1979 | Morris | A46B 3/005 15/167.1 |
| 4,248,214 | A | 2/1981 | Hannah | |
| 4,344,535 | A * | 8/1982 | Cagnazzi | A45D 44/18 132/308 |
| 4,432,758 | A | 2/1984 | Finegold | |
| 4,553,959 | A | 11/1985 | Hickey | |
| 4,684,369 | A | 8/1987 | Wildemeersch | |
| 4,738,687 | A | 4/1988 | Galloway | |
| 4,773,901 | A | 9/1988 | Norton | |
| 4,935,017 | A | 6/1990 | Sylvanowicz | |
| 5,084,036 | A | 1/1992 | Rosenbaum | |
| 5,380,270 | A | 1/1995 | Ahmadzadeh | |
| 5,582,599 | A | 12/1996 | Daneshvar | |
| 5,699,574 | A * | 12/1997 | Oviatt | A45D 40/26 132/320 |
| 5,919,170 | A | 7/1999 | Woessner | |
| 6,063,063 | A * | 5/2000 | Harboe | A61F 2/0009 604/256 |
| 6,264,389 | B1 * | 7/2001 | Ducharme | B43K 23/08 401/107 |
| 6,926,708 | B1 | 8/2005 | Franks-Farah | |
| 7,867,220 | B2 | 1/2011 | Tanghoj | |
| 8,529,549 | B2 | 9/2013 | Tanghoj | |
| 2003/0004496 | A1 | 1/2003 | Tanghoj | |
| 2003/0060807 | A1 | 3/2003 | Tanghoj | |
| 2004/0107524 | A1 * | 6/2004 | Kazmi | A46B 17/04 15/184 |
| 2004/0158231 | A1 * | 8/2004 | Tanghoj | A61F 5/44 604/544 |
| 2005/0028570 | A1 * | 2/2005 | Parsons | B43K 25/026 70/16 |
| 2006/0116661 | A1 | 6/2006 | Tanghoj | |
| 2006/0289030 | A1 * | 12/2006 | Pho | A45D 44/18 132/309 |
| 2008/0015527 | A1 | 1/2008 | House | |
| 2010/0256580 | A1 | 10/2010 | Faber | |
| 2010/0324540 | A1 * | 12/2010 | Paulen | A61M 25/0017 604/544 |
| 2012/0110951 | A1 * | 5/2012 | van Groningen | A61M 25/002 53/425 |
| 2012/0165791 | A1 | 6/2012 | Lovmar | |
| 2013/0261608 | A1 | 10/2013 | Tanghoj | |
| 2015/0018803 | A1 * | 1/2015 | Tjassens | A61M 25/002 604/544 |
| 2016/0075169 | A1 * | 3/2016 | O'Connor | B43K 23/12 401/195 |

FOREIGN PATENT DOCUMENTS

| | | |
|---|---|---|
| WO | WO 2004/056414 | 7/2004 |
| WO | WO 2009/054720 | 4/2009 |

OTHER PUBLICATIONS

Total Body Relief and Hygiene for Travel, Home Health, and Life's Less Comfortable Moments dated Apr. 19, 2014, retrieved from http://www.biorelief.com/blog/self-cath-fits-in-your-pocket/.

* cited by examiner

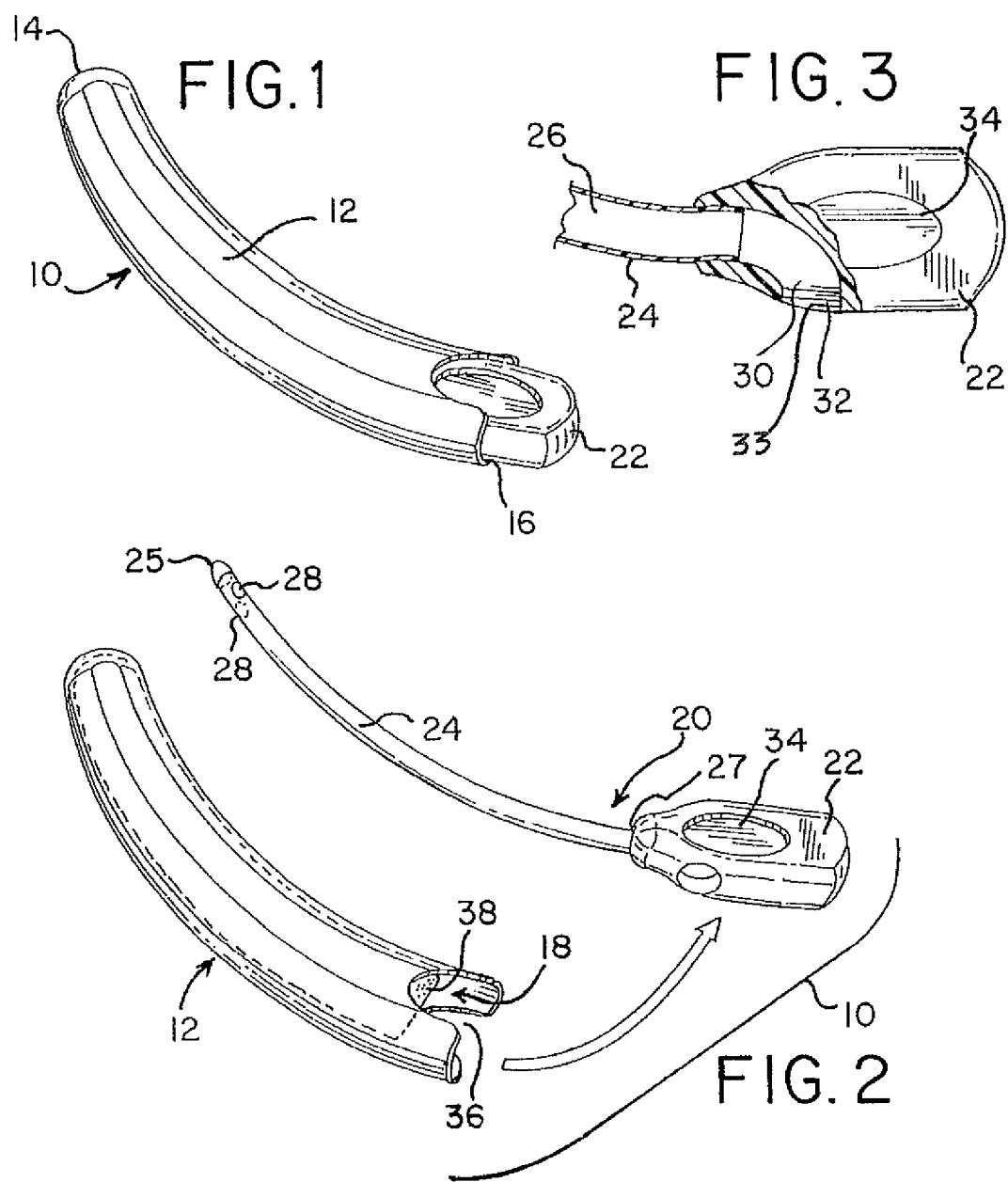
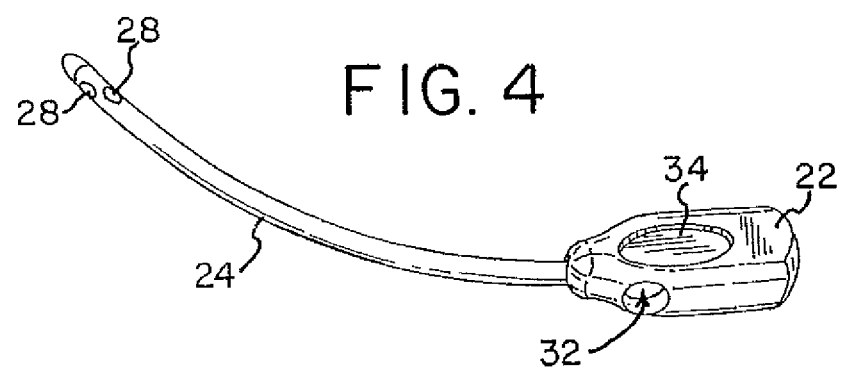

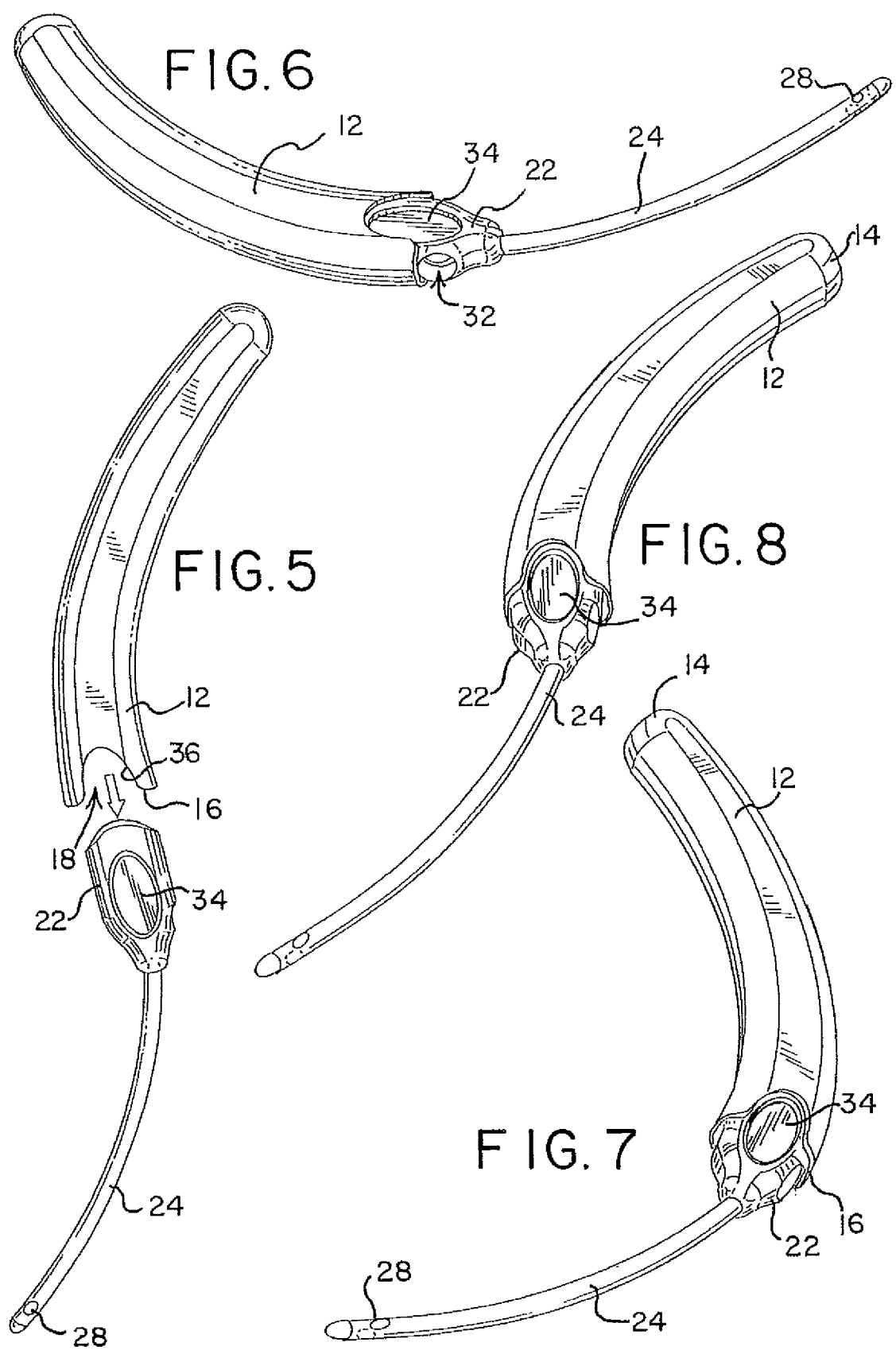

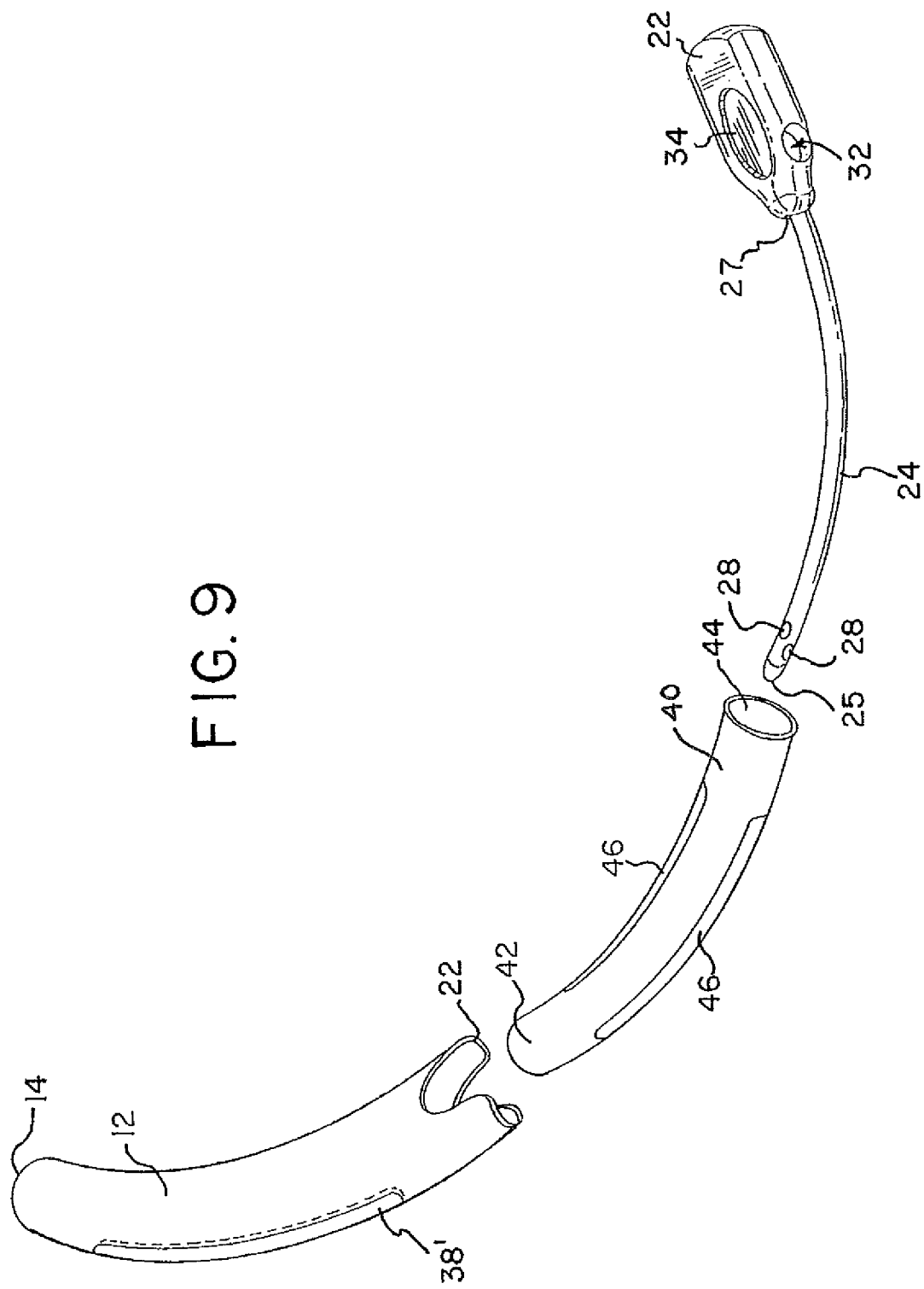

CURVED URINARY CATHETER

CROSS REFERENCE TO RELATED APPLICATIONS

This application is the U.S. National Stage of PCT International Patent Application No. PCT/US2015/050357, filed Sep. 16, 2015, which claims the benefit of and priority to U.S. Provisional Patent Application Ser. No. 62/051,666, filed Sep. 17, 2014, the contents of all of the above being hereby incorporated herein by reference in their entireties.

FIELD OF THE DISCLOSURE

The present disclosure is directed to urinary catheters and urinary catheter assemblies for humans and/or animals. More particularly, the present disclosure is directed to compact urinary catheters for females and pediatrics wherein the profile of the insertable portion of the catheter is curved and generally compliments the curvature of the female urethra while also aiding insertion due to the curved grip region. The catheter can be configured by the user to increase the gripping area of the assembly to allow for more ergonomical manipulation and insertion of the catheter.

BACKGROUND

Catheters are used to treat many different types of medical conditions and typically include an elongated catheter tube that is inserted into and through a passageway or lumen of the body. Urinary catheters and, in particular, intermittent urinary catheters are commonly used by individuals who suffer from certain abnormalities of the urinary system, such as urinary incontinence. With the advent of intermittent urinary catheters, individuals with problems associated with the urinary system can conveniently self-catheterize to drain the individual's bladder. Individuals who suffer from urinary incontinence will self-catheterize several times a day.

Self-catheterization involves removing the catheter assembly from its package and inserting and advancing the catheter tube through the user's urethra. In many cases, users of intermittent urinary catheters have limited or diminished dexterity that is often the result of spinal cord injuries. Users of intermittent catheters are often required to self-catheterize outside the privacy of the home, such as in public restrooms. Thus, for these and other reasons, it is desirable that the intermittent catheters are provided in discreet packaging that is easy to open, compact and portable.

In addition to the desire for discreet packaging, portability and compactness, ease of handling and patient comfort during insertion of the catheter into the urethra are also goals of urinary catheter manufacturers. Properly positioning the catheter, manipulating the catheter and advancing the catheter in a way that limits or avoids discomfort and irritation to the urethral canal is not without its challenges. Thus, it would be desirable to provide a catheter and catheter assembly that can accommodate different ways of grasping the assembly in accordance with the user's preference. It would also be desirable to provide a compact catheter wherein the insertable portion is pre-configured to compliment the shape of the urethra and, more particularly, the female urethra. It would also be desirable to provide a combined catheter and handle that includes a curved angle of insertion for a female user that is in accordance with the female anatomy, and also allows for insertion in a difficult to view manner (i.e., "blinded insertion").

SUMMARY

In one aspect, the present disclosure is directed to a urinary catheter assembly. The urinary catheter assembly includes an elongated housing that has a closed proximal end, an open distal end and wherein the housing defines a catheter chamber. The catheter assembly also includes a catheter subassembly that has a gripping member and a catheter tube extending therefrom. The gripping member includes an internal flow path in flow communication with the flow path of the catheter tube and an outlet in the gripping member. The gripping member and the open distal end of the housing are mutually sized and shaped to fixedly retain the gripping member whereby in a first configuration the catheter tube is concealed within the chamber and whereby in a another configuration the catheter extends away from the housing.

In another aspect, the present disclosure is directed to a catheter assembly that includes a handle that has a closed proximal end, an open distal end. The handle has a non-linear profile of a selected curvature. The catheter assembly also includes a catheter subassembly carried by the handle. The catheter subassembly includes a gripping member attached to the handle at the open distal end and a catheter tube that extends from the gripping member in a direction away from the handle.

In a more particular aspect, the catheter assembly may define a generally continuous curved profile wherein the catheter tube extends from said gripping member in the same directional curve as the handle. Alternatively, the catheter assembly may define a profile wherein the catheter tube extends from the gripping member in a direction that curves away from the curvature of the handle.

BRIEF DESCRIPTION OF THE DRAWINGS

FIG. 1 is a perspective view of the catheter assembly in accordance with the present disclosure;

FIG. 2 is a perspective view of the catheter assembly in accordance with the present disclosure with the catheter subassembly separate from the housing/handle;

FIG. 3 is an enlarged side view of the gripping member of the catheter assembly in accordance with the present disclosure with a portion of the gripping member broken away;

FIG. 4 is a perspective view of the catheter subassembly;

FIG. 5 is a perspective view of the catheter assembly of the present disclosure with the catheter subassembly being detached from the housing/handle;

FIG. 6 is a perspective view of the catheter assembly in one embodiment of a deployable configuration;

FIG. 7 is a different perspective view of the catheter assembly of FIG. 6;

FIG. 8 is a perspective view of the catheter assembly in another embodiment of a deployable configuration; and FIG. 9 is an exploded view of an embodiment of a catheter assembly including a hydration liner.

DETAILED DESCRIPTION OF THE EMBODIMENTS

The present disclosure is directed to urinary catheters and, in particular, urinary catheters for females that are compact when in their undeployed condition. The catheter assemblies disclosed herein may include a catheter subassembly that can be removed from a housing and mounted onto the housing to provide the user with an enlarged handling or grasping area. Catheter assemblies of the type disclosed herein typically include a curved catheter tube that substantially compliments the curvature of the female urethra. The catheter assemblies disclosed herein also allow the user (typically female) to adapt the assembly for different use positions.

FIG. 1 shows a catheter assembly in accordance with the present disclosure. As shown in FIG. 1, catheter assembly 10 includes a housing 12 having a proximal end 14 and an open distal end 16. Housing 12 defines an interior chamber 18 (shown in FIG. 3) for receiving at least the catheter tube of a catheter subassembly described further below. Housing 12 is preferably made of a light-weight, relatively rigid polymeric material. Preferably, the polymeric material is a relatively rigid material that protects the contents of the catheter assembly 10. The polymeric material also may have a low Moisture Vapor Transmission Ratio (MVTR). In addition, it is preferable that the polymeric material of housing 12 be non-transparent and opaque (and, for example, available in different colors), such that the contents of housing 12 cannot be easily identified. Polymeric materials that are suitable for use in housing 12 include polyvinyl chloride, polycarbonate, nylon, ABS and polyethylene. As noted earlier, catheter assembly 10 is preferably of a compact size, which is suitable for transporting in a purse, a small pouch, or on the person in a discreet manner.

Catheter subassembly 20 includes a base or gripping member 22. At least a portion of gripping member 22 may likewise be made of a suitable polymeric material, such as the polymeric material used for housing 12 as described above. Extending from gripping member 22 is a catheter tube 24. Catheter tube 24 includes a proximal end 25 and a distal end 27 attached to gripping member 22. The terms "distal" and "proximal" are used throughout this disclosure. When used in the context of the catheter tube that is inserted into the body of the user, the term "proximal" is used to refer to that end or portion of the catheter tube that during use is closer in proximity to the user's body and/or initially enters the user's body upon insertion. The term "distal" is used to refer to an end or portion of the catheter tube that is opposite the proximal end or portion and is typically further away from the user's body. For the sake of consistency, when the terms "distal" and "proximal" are used in the context of a housing that receives the catheter tube such as housing 12 described above and shown in the Figures, which are not intended for introduction into the user's body, a proximal end or proximal portion is that end or portion closer to the proximal end of the catheter tube when the catheter tube is housed within such housing, while the distal end or portion is located opposite to such proximal end or portion. Catheter tube 24 defines an internal flow path 26 for transporting urine therethrough. Catheter tube 24 includes eyelets 28 at or near the proximal end of catheter tube 24 for receiving liquid flow and communicating liquid (e.g., urine) to flow path 26.

Catheter tube 24 may be made of a biocompatible polymeric material having sufficient stiffness that it can be provided in and maintain a curved profile as shown in the Figures. The material should be such that catheter tubes made therefrom can be easily inserted into the body of the user, yet flexible enough to avoid causing pain or discomfort to the user and to allow for movement within the urinary canal. Materials that are suitable for use as catheter tube 24 include polyvinyl pyrrolidone (PVP), polyamide, polyanhydride, polyether, poly(ether imide), poly(ester imide), polyvinyl alcohol, polyvinyl chloride, polycarbonate, poly($\varepsilon$-caprolactone) with polymethylvinylsiloxane, poly(ethylene-co-(vinylacetate)) with dicumylperoxide, poly(D-lactide), poly(L-lactide), poly(DL-lactide) and poly(glycolide-co-($\varepsilon$-caprolactone))-segments, multiblock copolyesters from poly ($\varepsilon$-caprolactone) and PEG and chain extender based on cinnamic acid groups, poly($\varepsilon$-caprolactone) dimethacrylate and n-butyl acrylate, oligo($\varepsilon$-caprolactone) diols, oligo (p-dioxanone) diols and diisocyanate, linear density polyethylene, linear low density polyethylene, high density polyethylene, and polypropylene. Catheter tube 24 may also be entirely made of a hydrophilic material or a material that has been made hydrophilic. Additional details of such hydrophilic catheters and activation thereof are described in U.S. Pat. No. 8,051,981, which is incorporated herein by reference.

As seen in FIG. 3, flow path 26 of catheter tube 24 communicates with an internal flow path 30 of gripping member 22. Flow path 30 of gripping member 22 terminates in outlet 32. Outlet 32 is preferably located on gripping member 22 in a location where, during use, urine flowing through flow path 30 of gripping member 22 will be directed toward the toilet. For example, as shown in FIG. 3, flow path 30 gradually curves approximately 45-90° from the point where it receives the distal end of catheter tube 24 to the point where it terminates in outlet 32. This allows the (female) user in a typical self-catheterizing position to direct and insert the curved catheter tube into her urethra with outlet 32 open to urine receptacle (e.g., toilet), thereby allowing for direct drainage of urine into the receptacle. Outlet 32 may include an inner surface, such as a threaded surface 33 or other surface to which an external urine collection bag may optionally be attached to the gripping member at outlet 32.

As shown in FIGS. 1-3, at least a portion of gripping member 22 may include a textured or other roughened gripping surface or region 34. In one embodiment, gripping surface 34 may be provided as a defined region of gripping member 22. In that regard, housing 12 may include a cutout portion 36 which leaves the gripping surface 34 exposed and accessible for grasping by the user.

Housing 12 may further include a hydration element 38 or other element for making tube 24 more lubricious contained within chamber 18 of housing 12, as shown in FIG. 2. Hydration element 38 contains an agent that may activate the hydrophilic coating of catheter tube 24, thereby making tube 24 more lubricious. In one embodiment, hydration element 38 may be provided as a sealed sachet or pillow 38 that includes water or other aqueous solution within it. Hydration element 38 may be secured to the wall of interior chamber 18 or freely placed within chamber 18.

In one embodiment, hydration element 38 may preferably be made of a suitable material that is selected to release the hydrating agent, such as water vapor, through its walls. In addition, the hydration element may include an insert made of a material that retains water or other aqueous solution. In one embodiment, the insert may be made of calcium carbonate, while the walls of the hydration element containing the insert may be made of a polymeric material that is vapor permeable but liquid impermeable.

In another embodiment, the system of hydrating or for otherwise making tube 24 more lubricious may include a liner or sleeve 40 received by housing 12. As shown in FIG. 9, liner 40 may be a substantially cylindrical tube closed at its proximal end 42 with an opening 44 at its distal end for receiving catheter tube 24. Liner 40 may be curved similarly to housing 12 and catheter tube 24 to be received by housing 12 and receive catheter tube 24, respectively. Liner 40 may include windows 46 that allow for passage of liquid or vapor and contact with catheter tube 24. Where vapor hydration is used to make the catheter tube more lubricious, a vapor-providing medium may be provided between the outer surface of liner 40 and the inner surface of housing 12. Windows 46 may be covered with a water-impermeable, vapor permeable material to allow for the passage of (water) vapor. The vapor-providing medium may be an amount of liquid (e.g., water) in the space between the outer surface of liner 40 and inner surface of housing 12, or an insert that retains an amount of water or other liquid, as described above.

In yet another embodiment, a lubricating gel may be provided with a closed liner (without windows) or other compartment, such as a gel grommet, that resides within housing 12 and receives at least a portion of catheter tube 24. Liner and gel lubricating systems which may be used in the catheter assemblies described above are also disclosed in International Patent Application No. PCT/US2015/033344, the contents of which is incorporated herein by reference.

As shown in the Figures, housing 12 may have a non-linear, curved profile. Likewise, catheter tube 24 may also have a non-linear, curved profile that is at least substantially identical to the curvature of housing 12. In an embodiment, catheter tube 24 is preferably molded, such as injection molded, or may be otherwise formed, such as by a combination of molding and extrusion to arrive at the non-linear, curved profile, as shown in the Figures. In accordance with the present disclosure, the curvature of catheter tube 24 may preferably compliment the curvature of the female urethra. In an embodiment, the curvature of catheter tube 24 substantially matches the curvature of housing 12.

Catheter assemblies of the present disclosure are capable of existing in several different and various conditions. Catheter assembly 10 may exist in a non-deployed condition, as generally shown in FIG. 1. In the non-deployed condition, catheter subassembly 20 is associated with housing 12, such that catheter tube 24 resides within chamber 18 of housing 12. Open distal end 16 of housing 12 and gripping member 22 are mutually sized and shaped so that catheter subassembly 20 may be retained by housing 12. Retention of gripping member 22 at the open distal end 16 of housing 12 may be by friction-fit or snap-fit.

In a second condition, catheter assembly 10 may be removed from housing 12 and deployed for use by the patient. From the first condition, the user simply pulls on gripping member 22 to release it from housing 12. Gripping surfaces 34 may be grasped by the user to separate catheter subassembly 20 from housing 12. The user may then, by using gripping member 22, manipulate and guide catheter tube 24 for insertion and advancement into the urethra. After catheterization, catheter tube 24 may be returned to chamber 18 and gripping member 22 may be fit into housing 12, as generally shown in FIG. 1. The used catheter assembly 10 may then be disposed of.

In a third condition, after removal of catheter assembly 20 from housing 12, catheter assembly may be mounted onto and carried by housing 12, such that catheter tube 24 extends away from housing 12, as shown in FIGS. 5, 6, 7 and 8. Again, as previously described, gripping member 22 is mutually sized and shaped with open distal end 16 such that gripping member can be mounted by press-fit onto housing 12 at open distal end 16 with the catheter tube 24 extending from and carried by housing 12. In this extended deployed condition, housing 12 also serves as an enlarged handle that can be more easily grasped by the user and better manipulated during insertion and advancement. In this regard, housing 12 may have a surface that improves gripping or grasping by the user. For example, housing 12 may include overmolded, rigid and soft sections in different textures and colors to aid in gripping and holding of catheter assembly 10.

As shown in FIG. 6, catheter subassembly 20 may be carried by handle 12 such that the profile of catheter assembly 10 is a continuous curve. In other words, when mounted on housing/handle 12, catheter tube 24 extends from gripping member 22 in the same directional curve as housing/handle 12. In such embodiment, the profile of the catheter assembly in the extended deployed condition resembles an open form of the letter "C" or is generally "C-shaped."

In an alternative configuration of the extended deployed condition, catheter subassembly 20 may be mounted on and carried by housing/handle 12 such that catheter tube extends from gripping member 22 in a direction that curves away from the curvature direction of handle/housing 12, as generally shown in FIG. 8. Thus, in this embodiment, the overall profile of catheter assembly 10 resembles an open form of the letter "S" or is generally "S-shaped."

The decision whether to mount catheter assembly 24 in the extended deployed condition in the "C" or "S" configuration may depend on user preference and what is more comfortable for the user when attempting to insert and advance catheter tube 24. Inasmuch as many users of urinary catheters may suffer from impaired dexterity, certain users may find a generally "C-shaped" catheter assembly easier to use than a generally "S-shaped" catheter assembly or vice-versa.

In either configuration described above, opening 19 in housing 12 and gripping member 22 are, as previously described, sized and shaped such that gripping member may be snugly press-fit into opening 19 while still leaving gripping surface 34 and outlet 32 (e.g., due to cut-out portion 36) outside of housing 12 during use such that the flow of urine is not obstructed and/or a collection container may be readily attached.

Other Aspects

Aspect 1: A urinary catheter assembly comprising: (a) an elongated housing comprising a closed proximal end, an open distal end, said housing defining a catheter chamber; and (b) a catheter subassembly comprising a gripping member and a catheter tube extending therefrom, said gripper member including an internal flow path in flow communication with said flow path of said catheter tube and an outlet, wherein said gripping member and said open distal end of said housing are mutually sized and shaped to fixedly retain said gripping member whereby in a first configuration said catheter tube is concealed within said chamber, and whereby in a second configuration said catheter tube extends away from said housing.

Aspect 2: The catheter assembly of Aspect 1 wherein said housing comprises a non-linear profile.

Aspect 3: The catheter assembly of Aspect 2 wherein said catheter tube has a non-linear profile that is substantially identical to said non-linear profile of said housing.

Aspect 4: The catheter assembly of any one of Aspects 1 through 3 wherein said gripping member includes a textured portion.

Aspect 5: The catheter assembly of any one of Aspects 2 through 4 wherein said catheter tube profile substantially matches the curvature of a female urethra.

Aspect 6: The catheter assembly of any one of Aspects 1 through 5 wherein said outlet comprises a port for attaching a collection container.

Aspect 7: The catheter assembly of any one of Aspects 1 through 6 further comprising a hydration element within said housing.

Aspect 8: The catheter assembly of Aspect 7 wherein said hydration element comprises a vapor providing material.

Aspect 9: A catheter assembly comprising: (a) a handle comprising a closed proximal end, an open distal end, said handle having a non-linear profile of a selected curvature; and (b) a catheter subassembly carried by said handle, said catheter subassembly comprising a gripping member attached to said handle at said open end and a catheter tube extending from said gripping member in a direction away from said handle.

Aspect 10: The catheter assembly of Aspect 9 wherein said catheter tube has a non-linear profile and a curvature that is substantially identical to said selected curvature of said handle.

Aspect 11: The catheter assembly of any one of Aspects 9 and 10 wherein said assembly defines a generally continuous curved profile wherein said catheter tube extends from said gripping member in the same directional curve as said handle.

Aspect 12: The catheter assembly of any one of Aspects 9 and 10 wherein said assembly defines a profile wherein said catheter tube extends from said gripping member in a direction that curves away from the curvature of said handle.

Aspect 13: The catheter assembly of Aspect 11 comprising a generally C-shape.

Aspect 14: The catheter assembly of Aspect 12 comprising a generally S-shape.

Aspect 15: The catheter assembly of any one of Aspects 9 through 14 wherein said catheter tube profile substantially matches the curvature of a female urethra.

Aspect 16: The catheter assembly of any one of Aspects 9 through 15 wherein said gripping member is releasable from said handle.

Aspect 17: The catheter assembly of any one of Aspects 9 through 16 wherein said handle defines a hollow interior chamber.

Aspect 18: The catheter assembly of Aspect 17 wherein said catheter tube is insertable into said chamber.

Aspect 19: The catheter assembly of any one of Aspects 17 through 18 wherein said handle further comprises a hydration element within said chamber.

Aspect 20: The catheter assembly of any one of Aspects 9 through 19 wherein said catheter tube defines a flow path and said gripping member comprises a flow path in communication with catheter tube flow path.

Aspect 21: The catheter assembly of Aspect 20 wherein said gripping member flow path terminates in an outlet.

Aspect 22: The catheter assembly of any one of Aspects 9 through 21 further comprising a flexible liquid collection container joined to said outlet.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A urinary catheter assembly comprising:
   a) an elongated housing comprising a closed proximal end, an open distal end, said housing defining a catheter chamber, wherein said housing comprises a non-linear profile; and
   b) a catheter subassembly comprising a gripping member and a catheter tube extending therefrom and defining a flow path, wherein said catheter tube has a non-linear profile that is substantially identical to said non-linear profile of said housing, said gripping member including an outlet and an internal flow path in flow communication with said flow path of said catheter tube and said outlet, wherein said gripping member and said open distal end of said housing are mutually sized and shaped to fixedly retain said gripping member whereby in a first configuration said catheter tube is concealed within said chamber, and whereby in a second configuration said catheter tube extends away from said housing.

2. The catheter assembly of claim 1 wherein said gripping member includes a textured portion.

3. The catheter assembly of claim 1 wherein said catheter tube profile is configured to substantially match the curvature of a female urethra.

4. The catheter assembly of claim 1 wherein said outlet comprises a port for attaching a collection container.

5. A catheter assembly comprising:
   a) a handle comprising a closed proximal end, an open distal end, said handle having a non-linear profile; and
   b) a catheter subassembly carried by said handle, said catheter subassembly comprising a gripping member, wherein said gripping member is attached to said handle at said open end in a first configuration whereby said catheter tube extends from said gripping member in a direction away from said closed proximal end of said handle or a second configuration whereby said catheter tube extends from said gripping member in a direction towards said closed proximal end of said handle.

6. The catheter assembly of claim 5 wherein said catheter tube has a non-linear profile substantially identical to said non-linear profile of said handle.

7. The catheter assembly of claim 5 wherein said catheter assembly comprises a generally C-shape in said first configuration.

8. The catheter assembly of claim 5 wherein said catheter assembly comprises a generally S-shape in said first configuration.

9. The catheter assembly of claim 5 wherein said catheter tube profile is configured to substantially match the curvature of a female urethra.

10. The catheter assembly of claim 5 wherein said gripping member is releasable from said handle.

11. The catheter assembly of claim 5 wherein said handle defines a hollow interior chamber.

12. The catheter assembly of claim 11 wherein said catheter tube is insertable into said chamber.

13. The catheter assembly of claim 11 wherein said handle further comprises lubricating element within said chamber.

14. The catheter assembly of claim 5 wherein said catheter tube defines a flow path and said gripping member comprises a flow path in communication with said catheter tube flow path.

15. The catheter assembly of claim 14 wherein said gripping member flow path terminates in an outlet.

16. The catheter assembly of claim 15 further comprising a flexible liquid collection container joined to said outlet.

\* \* \* \* \*